US011523980B2

(12) United States Patent
Mondon et al.

(10) Patent No.: US 11,523,980 B2
(45) Date of Patent: Dec. 13, 2022

(54) USE OF A PEPTIDE FOR THE TREATMENT OF EPIDERM

(71) Applicant: Sederma, Le Perray-en-Yvelines (FR)

(72) Inventors: Philippe Mondon, Montrouge (FR); Caroline Ringenbach, Le Perray-en-Yvelines (FR); Olga Gracioso, Le Perray-en-Yvelines (FR)

(73) Assignee: SEDERMA, Le Perray-en-Yvelines (FR)

( * ) Notice: Subject to any disclaimer, the term of this patent is extended or adjusted under 35 U.S.C. 154(b) by 43 days.

(21) Appl. No.: 17/044,721

(22) PCT Filed: Apr. 4, 2019

(86) PCT No.: PCT/EP2019/058551
§ 371 (c)(1),
(2) Date: Oct. 1, 2020

(87) PCT Pub. No.: WO2019/193113
PCT Pub. Date: Oct. 10, 2019

(65) Prior Publication Data
US 2021/0093537 A1  Apr. 1, 2021

(30) Foreign Application Priority Data

Apr. 5, 2018  (FR) .................................. 1852950

(51) Int. Cl.
*A61K 8/64* (2006.01)
*A61Q 19/00* (2006.01)

(52) U.S. Cl.
CPC ............... *A61K 8/64* (2013.01); *A61Q 19/00* (2013.01); *A61K 2800/21* (2013.01)

(58) Field of Classification Search
None
See application file for complete search history.

(56) References Cited

U.S. PATENT DOCUMENTS

| 8,404,648 | B2* | 3/2013 | Lintner | ................... | A61P 17/00 |
| | | | | | 514/21.9 |
| 8,450,456 | B2 | 5/2013 | Farra et al. | | |
| 2011/0033507 | A1* | 2/2011 | Lintner | ................... | A61Q 19/00 |
| | | | | | 530/331 |

FOREIGN PATENT DOCUMENTS

| FR | 2925501 A1 | 6/2009 |
| KR | 20150029884 A | 3/2015 |
| WO | 2007093839 A1 | 8/2007 |
| WO | 2010082175 A2 | 7/2010 |
| WO | 2014080376 A2 | 5/2014 |
| WO | 2015181688 A1 | 12/2015 |

OTHER PUBLICATIONS

International Search Report and Written Opinion for International Application No. PCT/EP2019/058551, dated Jun. 14, 2019, 9 pages.

* cited by examiner

*Primary Examiner* — Dominic Lazaro
(74) *Attorney, Agent, or Firm* — RatnerPrestia

(57) ABSTRACT

A peptide having the general Formula (1)

$$X\text{-}(Xaa)_n K^*TFK^*\text{-}(Xaa)_m\text{-}Z \qquad (1)$$

is described, where the peptide helps preserve or improve the condition of the epidermis and wherein X, $(Xaa)_n$, $(Xaa)_m$, n, m, K* and Z are as defined.

26 Claims, No Drawings
Specification includes a Sequence Listing.

SEQUENCE LISTING

```
<160> NUMBER OF SEQ ID NOS: 24

<210> SEQ ID NO 1
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 1

Lys Thr Thr Lys Ser
1               5

<210> SEQ ID NO 2
<211> LENGTH: 4
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 2
```

Gly Gln Pro Arg
1

<210> SEQ ID NO 3
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 3

Val Gly Val Ala Pro Gly
1               5

<210> SEQ ID NO 4
<211> LENGTH: 4
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Xaa being a lysine, ornithine, diaminobutyric
      acid, diaminopropionic acid or an hydroxylated derivative thereof
<220> FEATURE:
<221> NAME/KEY: MOD_RES
<222> LOCATION: (1)..(1)
<223> OTHER INFORMATION: X = -CO-R1 or -SO2-R1 or biot group, R1 =
      C1-C24 group
<220> FEATURE:
<221> NAME/KEY: MOD_RES
<222> LOCATION: (4)..(4)
<223> OTHER INFORMATION: Z = -OR1, -NH2, -NHR1 ou -NR1R2 ; R1, R2 =
      C1-C24 group
<220> FEATURE:
<221> NAME/KEY: MISC_FEATURE
<222> LOCATION: (4)..(4)
<223> OTHER INFORMATION: Xaa being a lysine, ornithine, diaminobutyric
      acid, diaminopropionic acid or an hydroxylated derivative thereof

<400> SEQUENCE: 4

Xaa Thr Phe Xaa
1

<210> SEQ ID NO 5
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 5

Lys Thr Phe Lys
1

<210> SEQ ID NO 6
<211> LENGTH: 4
<212> TYPE: PRT
<213> ORGANISM: artificial sequence
<220> FEATURE:
<223> OTHER INFORMATION: synthetic peptide

```
<400> SEQUENCE: 6

Arg Ser Arg Lys
1

<210> SEQ ID NO 7
<211> LENGTH: 4
<212> TYPE: PRT
<213> ORGANISM: artificial sequence
<220> FEATURE:
<223> OTHER INFORMATION: synthetic peptide

<400> SEQUENCE: 7

Gly Gln Pro Arg
1

<210> SEQ ID NO 8
<211> LENGTH: 4
<212> TYPE: PRT
<213> ORGANISM: Artificial sequence
<220> FEATURE:
<223> OTHER INFORMATION: Synthetic peptide

<400> SEQUENCE: 8

Lys Thr Ala Lys
1

<210> SEQ ID NO 9
<211> LENGTH: 4
<212> TYPE: PRT
<213> ORGANISM: Artificial sequence
<220> FEATURE:
<223> OTHER INFORMATION: Synthetic peptide

<400> SEQUENCE: 9

Lys Ala Tyr Lys
1

<210> SEQ ID NO 10
<211> LENGTH: 4
<212> TYPE: PRT
<213> ORGANISM: Artificial sequence
<220> FEATURE:
<223> OTHER INFORMATION: Synthetic peptide

<400> SEQUENCE: 10

Lys Phe Tyr Lys
1

<210> SEQ ID NO 11
<211> LENGTH: 5
<212> TYPE: PRT
<213> ORGANISM: artificial sequence
<220> FEATURE:
<223> OTHER INFORMATION: synthetic peptide

<400> SEQUENCE: 11

Lys Thr Thr Lys Ser
1               5

<210> SEQ ID NO 12
<211> LENGTH: 6
<212> TYPE: PRT
<213> ORGANISM: artificial sequence
<220> FEATURE:
<223> OTHER INFORMATION: Synthetic peptide
```

```
<400> SEQUENCE: 12

Gly Lys Thr Thr Lys Ser
1               5

<210> SEQ ID NO 13
<211> LENGTH: 6
<212> TYPE: PRT
<213> ORGANISM: artificial sequence
<220> FEATURE:
<223> OTHER INFORMATION: synthetic peptide

<400> SEQUENCE: 13

Val Gly Val Ala Pro Gly
1               5

<210> SEQ ID NO 14
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: amidation by a Elaidoyl chain on the N terminal
      end

<400> SEQUENCE: 14

Lys Thr Ala Lys
1

<210> SEQ ID NO 15
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: amidation by a Elaidoyl chain on the N terminal
      end

<400> SEQUENCE: 15

Lys Ala Tyr Lys
1

<210> SEQ ID NO 16
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: amidation by a Elaidoyl chain on the N terminal
      end

<400> SEQUENCE: 16

Lys Phe Tyr Lys
1

<210> SEQ ID NO 17
<211> LENGTH: 5
<212> TYPE: PRT
<213> ORGANISM: artificial sequence
<220> FEATURE:
<223> OTHER INFORMATION: synthetic peptide
```

```
<220> FEATURE:
<221> NAME/KEY: MOD_RES
<222> LOCATION: (1)..(1)
<223> OTHER INFORMATION: amidation by a Palmitoyl chain on the N
      terminal end
<220> FEATURE:
<221> NAME/KEY: MISC_FEATURE
<222> LOCATION: (5)..(5)
<223> OTHER INFORMATION: Xaa being either a Proline P or a Leucine L.

<400> SEQUENCE: 17

Tyr Gly Gly Phe Xaa
1               5

<210> SEQ ID NO 18
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end

<400> SEQUENCE: 18

Gly Lys Thr Thr Lys Ser
1               5

<210> SEQ ID NO 19
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: amidation by a Palmitoyl chain on the N
      terminal end
<220> FEATURE:
<221> NAME/KEY: MISC_FEATURE
<222> LOCATION: (6)..(6)
<223> OTHER INFORMATION: Xaa being Trp, Phe, Tyr, Tic, 7-hydroxy-Tic or
      Tpi

<400> SEQUENCE: 19

His Leu Asp Ile Ile Xaa
1               5

<210> SEQ ID NO 20
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Acetylation on the N-terminal end

<400> SEQUENCE: 20

Glu Glu Met Gln Arg Arg
1               5

<210> SEQ ID NO 21
<211> LENGTH: 5
<212> TYPE: PRT
<213> ORGANISM: artificial sequence
<220> FEATURE:
```

```
<223> OTHER INFORMATION: synthetic peptide

<400> SEQUENCE: 21

Tyr Ala Gly Phe Leu
1               5

<210> SEQ ID NO 22
<211> LENGTH: 4
<212> TYPE: PRT
<213> ORGANISM: artificial sequence
<220> FEATURE:
<223> OTHER INFORMATION: synthetic peptide

<400> SEQUENCE: 22

Ala His Ser His
1

<210> SEQ ID NO 23
<211> LENGTH: 6
<212> TYPE: PRT
<213> ORGANISM: artificial sequence
<220> FEATURE:
<223> OTHER INFORMATION: synthetic peptide

<400> SEQUENCE: 23

Ser Ile Lys Val Ala Val
1               5

<210> SEQ ID NO 24
<211> LENGTH: 6
<212> TYPE: PRT
<213> ORGANISM: artificial sequence
<220> FEATURE:
<223> OTHER INFORMATION: synthetic peptide

<400> SEQUENCE: 24

Gly Pro Gln Gly Pro Gln
1               5
```

USE OF A PEPTIDE FOR THE TREATMENT OF EPIDERM

CROSS REFERENCE TO RELATED APPLICATIONS

This application is the National Stage filing of International Application No. PCT/EP2019/058551, filed Apr. 4, 2019, and claims priority to FR 1852950, filed Apr. 5, 2018, both of which are incorporated herein by reference for all purposes.

TECHNICAL FIELD

The present invention relates to a cosmetic or dermatological peptide-based treatment, a new cosmetic or dermatological ingredient based on this peptide and compositions comprising it. It relates more particularly to a peptide for the treatment of the skin and its appendages, of human or animal mammals.

It concerns in particular the industries of cosmetic products, dermatological products and hygiene and personal care products.

BACKGROUND ART

Peptides have an important signal function and coordinate many biochemical processes. As a result, they have long become essential and promising active ingredients, particularly in the cosmetics industry, where new compounds are constantly being searched for, that are able to beautify the skin and the appendages, that is to say to improve their general condition.

Most of the peptides that are currently proposed are peptides acting on the dermis via the stimulation of the extracellular matrix components, mainly collagen and elastin. Numerous peptides are proposed in this axis, in particular by the Applicant, such as the Pal-KTTKS (SEQ ID NO 1) sold under the MATRIXYL® tradename, the mixture comprising the Pal-GHK and the Pal-GQPR (SEQ ID NO 2) sold under the MATRIXYL® 3000 tradename, the Pal-KMO2K sold under the MATRIXYL®synthe'6® tradename (MO2 corresponding to a dioxygenated methionine) or more recently the Pal-K(P)HG (having a proline grafted on the lysine) sold under the MATRIXYL®Morphomics® tradename, the Pal-VGVAPG (SEQ ID NO 3) sold under the Dermaxyl™ or Biopeptide EL™ tradenames or the N-acetyl-Tyr-Arg-O-hexadecyl sold under the Idéalift™ or Calmosensine™ tradenames.

Beauty and good health of skin depend to a large extent on the quality and thickness of the epidermis, especially through optimal differentiation of keratinocytes and the ability of the epidermis to form its outermost layer, the *Stratum corneum*, and through the regularly renewal of said outermost layer by desquamation. The epidermis and in particular the *Stratum corneum* form indeed a real cutaneous barrier essential to protect ourselves from molecules and aggressions (luminous radiation, pollutants, etc.) of the external environment. For example, a good protection of this skin barrier will advantageoustly limit the risk of microinflammation of the epidermis which can cause premature aging of the skin, protection above all necessary for sensitive skin. It also limits the risk of water loss which helps maintain good moisturisation of the epidermis.

SUMMARY OF THE INVENTION

The present invention aims to provide a peptide having an activity on the properties of the epidermis, in particular the *Stratum corneum*, that is to say a peptide capable of acting on the first layers on the surface of the skin.

For this purpose, according to a first aspect, the present invention provides a use of the peptide having the following general Formula 1:

$X\text{-}(Xaa)_n K^*TFK^*\text{-}(Xaa)_m\text{-}Z$ for a non-therapeutic cosmetic treatment to preserve or improve the condition of the epidermis. In the general Formula 1:

K* is selected in group comprising lysine, ornithine, diaminobutyric acid or diaminopropionic acid, or a hydroxylated derivative thereof, the two K* being identical or different;

$(Xaa)_n$ and $(Xaa)_m$, independently of each other correspond to a sequence of n or m amino acids Xaa chosen independently of one another from Gly, Ala, Pro, Val, Leu, Ile and Phe, with n and m being integers which may be equal or different between 0 and 5;

At the N-terminal end X is chosen from H, $-CO-R^1$, $-SO_2-R^1$ or a biotinoyl group;

At the C-terminal end Z is chosen from OH, $OR^1$, $NH_2$, $NHR^1$ or $NR^1R^2$; and Wherein $R^1$ and $R^2$ are, independently of one another, selected from an alkyl, aryl, aralkyl, alkylaryl, alkoxy, saccharide and aryloxy group, which may be linear, branched, cyclic, polycyclic, unsaturated, hydroxylated, carbonylated, phosphorylated, and/or sulfured, said group having 1 to 24 carbon atoms and may have in its backbone one or more O, S and/or N heteroatoms.

The peptide used according to the invention is thus characterized in that it contains at least the amino acid sequence K*TFK* that is biologically active on the epidermis. Sequences of 1 to 5 non-polar amino acids selected from Gly, Ala, Pro, Val, Leu, Ile and Phe may be added on either side of the active sequence K*TFK*, preferably selected from Gly, Ala, Pro, Val, preferably Gly and Ala. Preferably, according to the invention K* is lysine or ornithine, more preferably lysine. A preferred hydroxylated derivative is hydroxylysine.

More preferably according to the invention n and m are between 0 and 2, preferably are equal to 0, the peptide having the general Formula 2: X—K*TFK*—Z (SEQ ID NO 4)

Preferably, the peptide has the general Formula 3:

X—KTFK—Z

K being a lysine (Lys), T a threonine (Thr), F a phenylalanine (Phe), and X and Z being as defined above.

In vitro test results (on keratinocyte culture, skin explants or reconstructed skin) are given below in the description showing, thanks to the peptide according to the invention, a preservation/protection and an improvement of the condition of the epidermis, in particular by reinforcing the skin barrier function and harmonizing the natural process of maturation of the epidermis.

These tests have demonstrated a targeted action of the peptide according to the invention at several levels, in particular:

The peptide stimulates the production of several molecules constituting the cutaneous barrier or positively intervening in the differentiation of the keratinocytes at the origin of the barrier;

The peptide improves the moisturisation of the upper part of the epidermis;

The peptide improves the renewal of the *Stratum corneum* by desquamation;

The peptide stimulates the production of α-crystallin;

The peptide lowers the level of a number of molecules involved in skin microinflammations caused by multiple small daily aggressions (light radiation, pollutants, etc.).

In vivo test results given below in the description show thereafter real cosmetic benefits related to the peptide according to the invention: smoothing of the skin, better moisturisation (skin thus more transparent, supple and soft) and improved radiance and homogenization of the complexion. Thanks to the invention, skin defects are avoided or reduced.

Preferably, the peptide according to the invention is either modified at the N-terminal position or at the C-terminal position, the case X=H and Z=OH being excluded.

According to other preferred features of the invention:

$R^1$ and/or $R^2$ is an alkyl chain of 1 to 24 carbon atoms, preferably a lipophilic alkyl chain of 3 to 24 carbon atoms; and/or X is an acyl group CO—$R^1$; preferably selected from octanoyl ($C_8$), decanoyl ($C_{10}$), lauroyl ($C_{12}$), myristoyl ($C_{14}$), palmitoyl ($C_{16}$), stearoyl ($C_{18}$), biotinoyl, elaidoyl, oleoyl and lipoyl; more preferably selected from lauroyl ($C_{12}$), myristoyl ($C_{14}$) and palmitoyl ($C_{16}$), and/or Z is chosen from OH, OMe, OEt and $NH_2$, preferably OH; and/or X is chosen from palmitoyl ($C_{16}$), myristoyl ($C_{14}$) and lauroyl ($C_{12}$); more preferably palmitoyl ($C_{16}$) and Z is OH.

Peptides comprising at the N- or C-terminal position particular acid derivatives such as those of ascorbic, retinoic, cinnamic, oleanolic, hyaluronic, nicotinic, lipoic, gallic or pantothenic acid are also encompassed by the present invention.

A preferred peptide according to the invention is the Pal-KTFK—OH (also called Pal-KTFK, SEQ ID NO 5), corresponding to a palmitoyl chain substitution on the N-terminal end (X=Pal) and no substitution on the C-terminal end (Z=OH), of Formula 4:

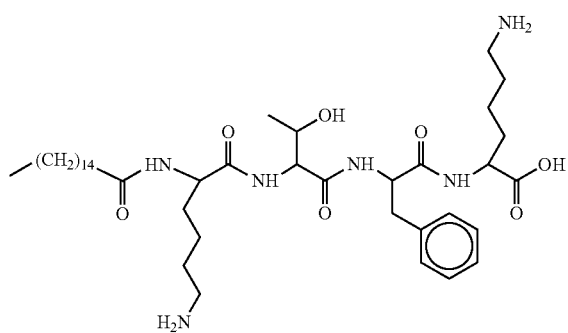

The peptide according to the invention may be optically pure or consist of L or D isomers or a mixture thereof. The naturally occurring L-isomers may be preferred. The peptide may be, if appropriate, in salt form, especially hydrochloride or acetate.

The present invention also covers derivatives of the peptide (with modification and/or addition of a chemical function but without change in the carbon skeleton) and analogs (with modification and/or addition of a chemical function but also with a change in the carbon skeleton), complexes with other species such as a metal ion (eg copper, zinc, manganese, magnesium, and others).

For its use according to the invention, the peptide may be solubilized in a physiologically acceptable lipophilic or hydrophilic matrix with, if appropriate, a solubilizer, depending on the envisaged galenic form.

By "physiologically acceptable medium" is meant according to the present invention, without limitation, an aqueous or hydroalcoholic solution, a water-in-oil emulsion, an oil-in-water emulsion, a microemulsion, an aqueous gel, an anhydrous gel, a serum, a dispersion of vesicles, a powder.

"Physiologically acceptable" means that the ingredients and compositions comprising the peptide of the invention are suitable for topical or transdermal use, in contact with mammalian mucous membranes, nails, scalp, hair, body hair and skin and more particularly human, compositions that can be ingested or injected into the skin, without risk of toxicity, incompatibility, instability, allergic response, and others. This "physiologically acceptable medium" forms what is conventionally called the excipient of the composition.

The peptide according to the invention may also be used in a vectorized form, by being bound, incorporated or adsorbed on/to macro-, micro- or nano-particles such as capsules, spheres, liposomes, oleosomes, chylomicrons, sponges, in the form of micro- or nano-emulsions, or adsorbed for example on organic powdery polymers, talcs, bentonites, spores or exines and other inorganic or organic supports.

Preferably, the peptide according to the invention is used in a particular form, "captured" in a microemulsion of oil-wax-surfactants and water so as to slow down its penetration and make it more bioavailable on the surface of the skin, at the level of the epidermis.

Thanks to this particular form, the peptide is substantially prevented from entering the dermis and can develop its biological action slowly and homogeneously as from the *Stratum corneum* and then in all levels of the epidermis.

According to a second aspect of the invention, there is provided a cosmetic or dermatological ingredient comprising the peptide of general Formula 1:

With in general Formula 1:

K* chosen from lysine, ornithine, diaminobutyric acid or diaminopropionic acid, or a hydroxylated derivative thereof, the two K* being identical or different;

$(Xaa)_n$ and $(Xaa)_m$, corresponding independently of one another to a sequence of n or m amino acids Xaa independently selected from Gly, Ala, Pro, Val, Leu, Ile and Phe, with n and m integers which may be equal or different in the range of 0 to 5;

At the N-terminal end X being chosen from H, —CO—$R^1$, —$SO_2$—$R^1$ or a biotinoyl group;

At the C-terminal end Z being chosen from OH, $OR^1$, $NH_2$, $NHR^1$ or $NR^1R^2$; and $R^1$ and $R^2$ being, independently of one another, selected from an alkyl, aryl, aralkyl, alkylaryl, alkoxy, saccharide and aryloxy group, which may be linear, branched, cyclic, polycyclic, unsaturated, hydroxylated, carbonylated, phosphorylated, and/or sulfurated, said group having 1 to 24 carbon atoms and may have in its backbone one or more O, S and/or N heteroatoms;

and a physiologically acceptable vehicle capable of slowing the penetration of said peptide into the skin to act on the epidermis.

The peptide is more precisely as defined above according to the first aspect of the invention. Preferably, the vehicle or vector is a microemulsion of oil-wax-surfactants and water in which the peptide is solvated, more preferably comprising a waxy phase containing lecithin.

In the formed microemulsion, the peptide find itself "trapped" by solvation through the establishment of weak bonds of ionic, hydrogen and Van der Vals between the peptide and the wax particles and via the surfactants.

The force and energy then induced during topical application allow the release of the peptide in the *Stratum corneum* by slow and gradual desolvation by breaking these weak bonds.

According to a third aspect of the invention, there is provided a cosmetic or dermatological composition comprising the ingredient according to the second aspect of the invention.

A composition comprising the peptide according to the invention, in particular according to the third aspect of the invention, is the one that will ultimately be applied by the user.

The composition may be provided in any galenical form (examples are given below in the description) and also be conveyed via a textile support of natural or synthetic fibers, wool, or any material adapted to come into contact with the skin, or which may be used in clothing, such as day or night underwear, handkerschieves, or tissues, in order to exert its cosmetic or dermatological effect through this skin/textile contact and allow continuous topical delivery.

In a particular and advantageous manner, according to the invention, the peptide may be associated with at least one additional active agent adapted to act as a reinforcement of activity and/or to act in a complementary manner on one or more other activities.

Various additional actives for this purpose are mentioned below in the detailed description.

According to a fourth aspect, the present invention provides a method for improving the aesthetic appearance of the skin comprising topically applying to the skin an effective amount of a cosmetic or dermatological composition according to the third aspect of the invention described above.

According to a fifth aspect, the present invention proposes a kit for producing a self-tanning cosmetic treatment comprising in separate compartments:

a) a composition according to the invention as defined above or a composition comprising in a physiologically acceptable medium the peptide according to the invention as defined above according to the first aspect;
b) a composition comprising in a physiologically acceptable medium a self-tanning active agent.

Particularly and advantageously, the peptide according to the invention can be used to achieve a natural soft smoothing prior to the application of a self-tanning active agent, the peptide being in particular applied for a period of at least 3 days, preferably 6 days, more preferably 8 days, prior to application of the self-tanning active.

According to the invention, by "topical treatment" or "topical use" is meant an application that is intended to act at the place where it is applied: skin, mucous membrane, appendages.

The peptide or the composition according to the invention containing it may be applied locally to the targeted zones.

The "effective" amount depends on various factors, such as age, condition of the patient, severity of the disorder or pathology, and the mode of administration. An effective amount means a non-toxic amount sufficient to achieve the desired effect.

In a cosmetic composition according to the invention, the peptide to be present in an effective amount, is generally in proportions of between 0.000001% and 5% relative to the total weight of the composition, preferably between 0.00001% and 0.1%, more preferably between about 0.0005 and 0.005%, depending on the destination of the composition and the desired effect more or less pronounced.

All percentages and ratios used in this application are by weight of the total composition and all measurements are made at 25° C., unless otherwise specified.

For example, for a cosmetic facial treatment, the European Cosmetics Directive has set a standard application amount of a cream of 2.72 $mg/cm^2$/day/person and for a body lotion of 0.5 $mg/cm^2$/day/person.

According to other features, the cosmetic treatment method according to the invention can be associated with one or more other treatment methods aimed at the skin, such as, for example, light therapy, heat, vibration, electroporation treatments, micro-needle patch, or aromatherapy.

According to the invention, devices can be proposed with several compartments or kits intended for the implementation of the method described above, and which could include, by way of example, and without being limiting, in a first compartment a composition comprising an active ingredient according to the invention and in a second compartment an additional excipient and/or active, the compositions contained in said first and second compartments being here considered as a combination composition for simultaneous, separate or spread over time use especially in one of the treatments defined above.

A composition according to the invention is suitable for a therapeutic treatment, in particular a treatment of the skin, in particular of a skin having a diseased epidermis.

According to a sixth aspect, a peptide for the cosmetic use, method, composition and kit according to the invention is provided, the peptide having the general Formula 1:

$$X\text{-}(Xaa)_n K^*TFK^*\text{-}(Xaa)_m\text{-}Z$$

wherein:

K* is selected in group comprising lysine (K), ornithine, diaminobutyric acid or diaminopropionic acid, or a hydroxylated derivative thereof, the two K* being identical or different;

(Xaa)n and (Xaa)m independently of each other correspond to a sequence of n or m amino acids Xaa chosen independently of one another from Gly, Ala, Pro, Val, Leu, Ile and Phe, with n and m being integers which may be equal or different between 0 and 5;

At the N-terminal end X is chosen from H, —CO—$R^1$, —$SO_2$—$R^1$ or a biotinoyl group;

At the C-terminal end Z is chosen from OH, $OR^1$, $NH_2$, $NHR^1$ or $NR^1R^2$; and Wherein $R^1$ and $R^2$ are, independently of one another, selected from an alkyl, aryl, aralkyl, alkylaryl, alkoxy, saccharide and aryloxy group, which may be linear, branched, cyclic, polycyclic, unsaturated, hydroxylated, carbonylated, phosphorylated, and/or sulfur, said group having 1 to 24 carbon atoms and may have in its backbone one or more O, S and/or N heteroatoms, the peptides Pal-KTFK—OH and Ela-KTFK—OH being excluded.

According to preferred features of the peptide:

K* is a lysine K or an ornithine; and/or n and m are independently one of the other 0 or 1 or 2; and/or the peptide is either modified in the N-terminal position or in the C-terminal position, the case where X=H and Z=OH being excluded; and/or $R^1$ and/or $R^2$ is an alkyl chain of 1 to 24 carbon atoms; and/or X is an acyl group CO—$R^1$ and Z is selected from OH, OMe, OEt and $NH_2$; and/or The peptide is solvated, preferably in a vehicle or vector which is a microemulsion of oil-wax-surfactants and water in which the peptide is solvated, more preferably comprising a waxy phase containing lecithin.

DETAILED DESCRIPTION

The present invention will be better understood in the light of the following description of an embodiment and in vitro and in vivo tests.

A) Preparation Example of the Pal-KTFK Peptide (SEQ ID NO 5) According to the Invention The Pal-KTFK peptide is prepared by peptide synthesis. A lysine is coupled with a resin via its terminal acid function (with a coupling agent, for example DCC (diclyclohexyl-carbodiimide)/NHS (N-hydroxysuccinimide) or HBTU (2-(1H-benzotriazol-1-yl)-1,3,3-tetramethyluronium hexafluorophosphate)/HOBT (1-hydroxy-benzotriazole)). The lysine thus protected is then reacted with a threonine derivative in the presence of a coupling agent, then the same operation is carried out to add the phenylalanine, and likewise to add the second lysine. The latter is then acylated on its amine function with an activated palmitic acid derivative (palmitoyl chloride for example) in the presence of a base. The peptide chain is cleaved from the resin in an acid medium and after precipitation, washing and drying, the palmitoyl-lysyl-threonyl-phenylalanyl-lysine product is obtained in solid form.

B) Preparation Example of a Cosmetic Active Ingredient According to the Invention Comprising the Pal-KTFK (SEQ ID NO 5)

The Pal-KTFK peptide is amphiphilic, the Pal chain being hydrophobic and the phenylalanyl part being hydrophilic. The peptide is solubilized in a water/glycol matrix with suitable surfactants.

C) Preparation Example of a Cosmetic Active Ingredient According to the Invention with a Vectorised Peptide Protocol:
Step 1: Preparation of an «Excipient» Phase:
An aqueous phase: water+a surfactant
+A wax phase: a wax+a lecithine based surfactant
+A oil phase: an oil+a surfactant
Strong agitation to form an oil-in-water emulsion. This step leads to a heterogeneous phase comprising a liquid part and a solid part comprising wax particles.
Step 2: Preparation of a phase comprising the active peptide according to the invention:
Aqueous phase: water+the Pal-KTFK peptide (200 ppm)
Step 3: Adding the «active» phase in the «excipient» phase under moderate agitation.
Step 4: Optionally adding one or more phases comprising a preservative in the final emulsion.

Step 5: Optionally adding in the final emulsion a pH adjuster (desired pH at approximately 4.5). The wax can be constituted of a plurality of wax, as well as for the oil.

Obtained Product:
In the emulsion formed, the peptide find itself "trapped" by solvation in the oil-in-water emulsion formed previously by virtue of the establishment of weak ionic, hydrogen and Van der Vals bonds between the peptide and the wax particles and via the lecithin.

The Pal-KTFK peptide is amphiphilic and therefore has a high affinity for inter-corneocyte cement in which it will diffuse and act uniformly after de-solvation.

D) In Vitro Efficacy Tests

They were conducted on the preferred peptide according to the invention, the Pal-KTFK, in its unsolvated form.

The following in vitro tests were performed on epidermal cells: normal human keratinocytes (NHK) or on skin explant or on reconstructed skin. The peptide according to the invention was tested, in solution in an inert solvent (ethanol), at recommended concentrations of use on the skin.

1/Improvement of the Epidermal Barrier and Harmonisation of the Epiderm Maturation The horny layer or *Stratum corneum* is an assembly of great complexity associating, on the one hand, flat, non-nucleated cells strongly bound to each other and, on the other hand, lipids and proteins whose composition and assembly ensure the unique properties of this structure highly resistant to physical, chemical and biological attacks of the environment.

The following tests show that the peptide according to the invention induces epidermal homeostasis and reinforcement of the cutaneous barrier, thanks assaying various markers involved in epidermal differentiation and barrier formation, on three different biological systems (thin layer culture of human keratinocytes or culture of human skin explants or reconstructed skin).

Keratinocytes mature gradually with a strong outer shell formed of proteins called involucrine and loricrin, interconnected through the intervention of transglutaminases, which are calcium sensitive enzymes. Other proteins in the maturation and homeostasis of the *Stratum corneum*, the SPRRs (Small Proline Rich Region Proteins), serve to strengthen this protein shell by creating flexible but strong cross-links between proteins, also via the activity of the transglutaminases. NICE-1 is a protein whose gene is located in the same place as those of many *stratum* proteins. Its composition makes it an ideal substrate for transglutaminases and resembles to that of loricrin. LECs (Late Cornified Envelope Proteins) are also among the last components to be bridged during the maturation phase. Furthermore, Keratins 10 and 1, as well as the ceramides, have a great importance in the formation and the quality of the *Stratum corneum* and its proteolipid matrix, hence the importance of cosmetic active stimulating their synthesis.

A good barrier function is also highly dependent on filaggrin and filaggrin-2 which are produced by keratinocytes where they undergo significant metabolism. They serve a time to stabilize the corneocyte by binding to the keratin and then end up being degraded into amino acids producing essential components of the natural moisturisation factor (NMF) found in the *Stratum corneum*. Water is also retained in the epidermis by the hyaluronic acid that surrounds the keratinocytes and acts as a real sponge, attracting and retaining up to 1000 times its weight in water.

Finally, α-crystallin is a small protein related to the HSP family (or heat shock proteins). It is present in the epidermis where it protects the epithelial cells, restores their mitochondrial functions and increases their resistance to oxidative stress. This protein possesses the property of being found in the cell and in its immediate vicinity. With its presence the skin is protected from UV, inflammatory and more generally oxidative type attacks.

1.1/DNA-Array

Principle:

The peptide according to the invention was contacted for 6 or 24 h with confluent KHN (n=3). Then the KHN mats were rinsed and the cells were crushed to extract their mRNAs. These mRNAs are then converted into small DNA sequences which are analyzed after deposition on DNA chips and amplification by a method similar to qRT-PCR (Real-Time Quantitative Reverse Transcription Polymerase Chain Reaction). The mRNA variations due to the peptide are compared to the control case (peptide solvent).

Results:

TABLE 1

Variation with respect to the control of the expression of genes coding for epidermal differentiation proteins. Effect of 4 ppm of the peptide according to the invention.

| Protein | Filaggrin | Filaggrin 2 | Loricrin | LCE3B | LCE3C | LCE3D |
|---|---|---|---|---|---|---|
| Variation | ×2.32 * | ×2.42 * | ×2.97 * | ×2.13 ** | ×3.25 ** | ×2.06 ** |

| Protein | LCE3E | LCE2D | SPRR2B | SPRR2C |
|---|---|---|---|---|
| Variation | ×2.33 ** | ×1.84 ** | ×2.13 ** | ×1.58 ** |

No toxic effects were noted.
* = 6 hours contact;
** = 24 hours contact

These tests show that several biological targets were induced early (6-24 h) in NHK in contact with the peptide according to the invention. The genes of loricrin, filaggrin and filaggrin 2, three proteins involved in the building of the corneocyte or the moisturisation of the *Stratum corneum*, were statistically better expressed than in the solvent control ($p<0.01$). Further qRT-PCR analysis on the expression of the filaggrin gene was conducted, and it was observed that the equivalent of 4 and 6 ppm of the peptide of the invention increased this expression by 2.87 and respectively. 3.66 times compared to control ($p<0.01$).

1.2/Study by LC-MS/MS (Liquid Chromatography Coupled with Mass Spectrometry)

Principle:

The same culture protocol as for the DNA-Array (1.1/ above) was used but with a longer culture time (7 days), the protein productions taking longer to be detected with this LC-MS/MS method. The NHK culture medium (n=3) was changed every 3 days. At the end of this contact, the cells were lysed so as to extract the proteins and to analyze them in the form of crushed material by a method associating the action of a protease on the crushed material, the separation of the fragments by coupled liquid chromatography to mass spectrometry, then the identification and concentration of pre-existing proteins according to the nature and quantity of fragments obtained (LC-MS/MS). To conduct LC-MS/MS analysis on equivalent amounts of protein, the protein concentration was measured on the crushed material.

A study of the variances and a Student's t test were carried out in order to judge the significance of the results.

Results:

TABLE 2

Variation with respect to the control of proteins related to the homeostatic maturation of the epidermis. Effect of 4 ppm of the peptide according to the invention.

| Protein | Filaggrin | NICE-1 | SPRR1A | Keratin 10 | α-cristallin |
|---|---|---|---|---|---|
| Variation | ×4.16 $p < 0.01$ | ×3.42 $p < 0.01$ | ×1.55 $p < 0.01$ | ×1.46 $p < 0.01$ | ×2.19 $p < 0.01$ |

No toxic effects were noted.

These results confirm that the peptide according to the invention induces positively the production of proteins related to differentiation: filaggrin, NICE-1 and SPRR1A, all three increased. In parallel, there is an increase in keratin-10, also known to be produced during epidermal differentiation phenomena. Keratin is used to strengthen the epidermis via desmosomes (intercellular junctions), favorably contributing to the homeostasis of the epidermis. control case, leading to complementary explorations.

Interestingly and unexpectedly, the expression of the α-crystallin protein appeared more important than in the

1.3/α-Cristallin on Reconstructed Skins

Principle:

Normal human fibroblasts were seeded in a matrix. A few days after keratinocytes were deposited on this equivalent dermis to form a uniform layer of cells. At this stage the whole was passed to an air-liquid interface (emersion) so as to form a pluristratified epidermis. After 21 days (approximately), a mature skin equivalent was obtained (with an epidermis comprising the *stratum corneum*).

On the eve of the emergence phase, the layer of confluent human keratinocytes of these skins received the peptide according to the invention for 24 hours and then for the following 18 days (period of formation of the epidermis). Cryo-sections (7 μm) were made and the α-crystallin was labeled with fluorescent antibodies (immunohistology). The fluorescence was analyzed in photos, an equivalent surface was analyzed for all the photographs (n=51-59). Student's t test was performed.

Results:

TABLE 3

Expression of α-crystallin protein in reconstructed skin epidermis. Effect of 4 and 6 ppm of the peptide according to the invention.

| Concentrations | α-cristallin % of variation/control |
|---|---|
| Control | Reference |
| 4 ppm | +61%; $p < 0.01$ |
| 6 ppm | +164%; $p < 0.01$ |

No toxic effects were noted.

These results show that the α-crystallin is very clearly stimulated in the skin thanks to the peptide according to the invention (+61 and +164% relative to the control, $p<0.01$). This protein is described to exert a protective effect of the keratinocyte present in the epidermis, its proteins and its mitochondria.

1.4/Regulation of Differentiation and Moisturizing Elements of the Epidermis

Principle:

Confluent NHKs (n=3) were cultured as previously for 7 days in the presence or absence (control) of the peptide according to the invention, then immunocytochemistry markings were carried out using antibodies directed against proteins characteristic of the maturation of the epidermis: involucrin, loricrin and filaggrin, or of moisturizing: filaggrin, as well as ceramides (structuring elements of the *Stratum corneum*).

The moisturizing aspect was evaluated by the assay of hyaluronic acid produced by keratinocytes by an ELISA method.

Finally, the influence of the peptide according to the invention on the activity of transglutaminases and on the expression of the transglutaminase-5 gene was evaluated.

For this, confluent NHKs were brought into contact with the peptide according to the invention up to 21 days. Transglutaminase activity was assessed using a protocol using fluorescent dansylcadaverine which is bound to *Stratum corneum* proteins by these enzymes. An analysis of the fluorescence was performed, and the results compared to the solvent control.

With regard to transglutaminase-5, a qRT-PCR was performed after 72 hours of contact between the KHN and the peptide according to the invention.

A quantification of the number of cells was carried out in parallel for the 4 tests described in this part, so as to reduce the results to the number of cells.

Results:

TABLE 4

Induction of involucrin, loricrin, filaggrin and ceramide formation in NHK (immunofluorescence). Effect of 2 ppm of the peptide according to the invention.

| Concentrations | Involucrin % of variation/ control | Loricrin % of variation/ control | Filaggrin % of variation/ control | Ceramides % of variation/ control |
| --- | --- | --- | --- | --- |
| Control | Reference | Reference | Reference | Reference |
| 2 ppm | +60%; $p < 0.05$ | +261%; $p < 0.01$ | +554%; $p < 0.01$ | +334%; $p < 0.01$ |

No toxic effects were noted.

These results show that the peptide according to the invention effectively promotes the maturation of NHKs. The effect is clear at 2 ppm.

TABLE 5

Induction of hyaluronic acid secretion in NHK. Effect of 4 and 6 ppm of the peptide according to the invention.

| Concentrations | Hyaluronic acid % of variatio/control |
| --- | --- |
| Control | Reference |
| 4 ppm | +40%; $p < 0.01$ |
| 6 ppm | +91%; $p < 0.01$ |

No toxic effects were noted.

These results show that the peptide according to the invention participates in the moisturisation of the epidermis.

TABLE 6

Variation in transglutaminase activity and transglutaminase-5 gene expression in KHN. Effect of 4 and 6 ppm of the peptide according to the invention.

| Concentrations | Intra-KHN activity % of variation/control | Gene expression % of variation/control |
| --- | --- | --- |
| Control | Reference | Reference |
| 4 ppm | +45%; $p < 0.01$ | +133%; $p < 0.01$ |
| 6 ppm | +107%; $p < 0.01$ | +798%; $p < 0.01$ |

These results show the effect of the peptide according to the invention on the expression of the transglutaminase-5 gene, known to bind inter alia the loricrin proteins, involucrin and thus contribute to forming the *Stratum corneum*. In parallel, there is indeed an increase in the activity of transglutaminase proteins in keratinocytes.

All these results, obtained by complementary methods, show that the contact of NHK with the peptide according to the invention induces stimulations of synthesis of key cellular constituents which lead to reinforcing the cutaneous barrier with respect to possible environmental and environmental aggressions and promote the moisturisation of the superficial layer of the epidermis.

1.5/Mechanism of Stimulation of Maturation: TRPC6

The TRPC6 receptor (Transient Receptor Potential Canonical 6) is involved in the calcium-induced keratinocyte differentiation. Its simple stimulation is enough to trigger the differentiation of the epidermis and then the construction of the structures necessary for the formation of a *stratum corneum*. TRPC6 is absent from the keratinocytes of the basal layer. It is specific to the mature parts of the epidermis.

The DNA-Array (cf.1.1 above) has revealed, in addition to the stimulation of the genes coding for the formation of the *Stratum corneum*, the increase in production of mRNA coding for TRPC6, a protein that provides intracellular calcium flux. This very significant increase related to the peptide according to the invention (4 ppm) was ×6.05, compared with the solvent control at 6 h.

Principle:

Confluent keratinocytes were loaded with a specific calcium probe. This molecule becomes very fluorescent in the presence of intracellular free calcium. The appearance of fluorescence under the microscope was monitored. The cells, once loaded, were rinsed and then received the peptide according to the invention at 6 or 15 ppm or a positive control (bradykinin).

A study of the variances and a t test of Student were carried out in order to judge the significance of the results (n=3 for each condition).

Results:

The visual results show that the peptide according to the invention indeed induces an intracellular calcium mobilization in the confluent keratinocytes (visible under a fluorescence microscope after about 30 minutes of contact between the cells and the peptide.) This calcium release mechanism is well known to promote the differentiation of keratinocytes by allowing the coordinated formation of the elements of the *Stratum corneum*.

1.6/Epigenetic Regulation of Maturation: ANCR

ANCR (Anti-differentiation NonCoding RNA) is a Lnc-RNA (long non-coding RNA) composed of 855 bases. It is essential for the homeostasis of the epidermis. It is overexpressed in its basal part and, on the contrary, strongly diminished in its differentiated and mature parts. ANCR is part of the complex network of mechanisms involved in the regeneration of the epidermis and in the formation of the epidermal barrier. Its experimental depletion in the keratinocyte triggers a differentiation of the latter with the expression of the early and final markers of epidermal maturation: filaggrin, loricrin, involucrin. This is an example of epigenetic regulation that applies to the formation of the cutaneous barrier.

Principle:

In this test confluent keratinocytes were contacted with the peptide according to the invention for 24 hours, then the cells were rinsed, ground and their RNAs were extracted, converted into DNA and then analyzed by qRT-PCR.

A study of the variances and a Student's t-test were carried out in order to judge the significance of the results (n=4 for each condition).

Results:

TABLE 7

Variation of the expression of Lnc-RNA ANCR at 24 h; effect of the peptide according to the invention (results in ratio vs control).

| Concentrations | ANCR ratio % of variation/control |
|---|---|
| Control | Reference |
| 4 ppm | −27%; p < 0.05 |
| 6 ppm | −34%; p < 0.01 |

These results show that the peptide according to the invention allows a moderate but dose-dependent and significant reduction of this Lnc-RNA, epigenetic regulator of epidermal differentiation.

1.7/Desmosomes

Desmosomes form plaques joining the keratinocytes to each other. These plates are very resistant. They are formed especially of desmoglein. They allow the intracellular anchoring of the keratin-10 filaments and participate in the cellular cohesion of the epidermis.

Principle:

Desmoglein was searched on sections of abdominal skin (female, Caucasian, 54 years old) who had received a cream containing 6 ppm of the peptide according to the invention or the placebo cream. After 6 days (cream applied daily), the skins were frozen and sectioned to look for desmoglein using antibodies against this protein (fluorescence immunohistology). Photos were captured using a fluorescence microscope and the images analyzed using suitable software. The results were compared to those of the placebo cream.

Results:

TABLE 8

Variation in desmogleine production at 6 days on an abdominal skin explant model; effectof the peptide according to the invention (results in ratio vs control).

| Concentrations | Desmogleine % of variation/control |
|---|---|
| Control | Reference |
| 6 ppm | +24%; p < 0.01 |

These results show that the formation of desmosomes is favored thanks to the peptide according to the invention since the expression of the desmoglein protein, an essential component of desmosomes, is significantly increased.

1.8/Effect on Desquamation

KLK5 (kallikrein 5) is an enzyme involved in the renewal of the *Stratum corneum* allowing natural desquamation, thus ensuring a soft natural polishing effect ("soft-polish").

Principle:

The same sections as those used for desmoglein, as well as the same method (fluorescence immunohistology) were used to analyze and quantify the effect of the peptide according to the invention on this desquamation marker.

Results:

TABLE 9

Variation in KLK5 production at 6 days on an abdominal skin explant model; effect of the peptide according to the invention (results in ratio vs control).

| Concentration | KLK5 % of variation/control |
|---|---|
| Control | Reference |
| 6 ppm | +258%; p < 0.01 |

The homeostasis of the skin requires in addition to the formation of an effective skin barrier, the possibility of ensuring the renewal of corneocytes by desquamation. A significant increase in KLK5 is observed with the peptide according to the invention, which is known to ensure a soft natural smoothing phenomenon.

2/Moderation of the Production of Inflammation Markers

The skin is subjected to constant stress (exposure to UV, smoke, pollutants, etc.), some of which causing a direct or indirect inflammatory response. The uncontrolled or constant inflammatory response, although of low intensity, induces the production of cytokines such as IL-1α, IL-1β, IL-6, TNFα, and lipids such as PGE2 to attract or stimulate other cells, causing reactions in cascades. The pro-inflammatory microenvironment thus formed modifies the homeostasis of the skin and gradually modifies or even destructs the biomolecules of the cells and tissues. Disruption of the skin barrier integrity is also induced. Thus, the mediators of inflammation, IL-6 and PGE-2, are known to give rise, via micro-inflammations, to premature aging phenomena. In addition, sensitive and irritated skin is characterized by an abnormally high secretion of cytokines, pro-inflammatory peptides (IL-1, IL-6 for example) and pro-inflammatory lipids (PGE-2 for example).

To test the active, keratinocytes were cultured under mild stress conditions (application of UVB radiation) so as to mimic experimental micro-inflammation of the skin. In this situation a significant decrease in their secretome of inflammation mediators will be interpreted in the sense of a repairing and protective action of the skin.

Principle:

NHKs in culture and at confluence were brought into contact with the peptide according to the invention (or its solvent) for 24 hours in a medium allowing their survival, then the mats were irradiated with UVB in a physiological buffer and placed back into contact with products to be tested for 24 hours. At the end of this incubation, the culture media were assayed by ELISA in order to know the quantities of pro-inflammatory mediators produced by these cells in response to irradiation. The results were compared with solvent control +/−irradiation. A cellular respiration test was conducted to evaluate the number of cells and standardize the results.

A study of the variances and a Student's t test were carried out in order to judge the significance of the results.

Results:

TABLE 10

Variation of the secretome of pro-inflammatory mediators by NHKs exposed to UVB. Effect of the peptide according to the invention.

| | % of variation/control | | | | |
|---|---|---|---|---|---|
| | TNF-α | IL-6 | PGE2 | IL-1α | IL-1β |
| Solvent control solvant without UVB | Reference | Reference | Reference | Reference | Reference |
| Solvent control, UVB | +2527% $p < 0.01$ | +2720% $p < 0.01$ | +407% $p < 0.01$ | +104% $p < 0.01$ | +269% $p < 0.01$ |
| 2 ppm | −10% dns | −12% dns. | −31% $p < 0.01$ | −15% dns | −14% dns |
| 4 ppm | −56% $p < 0.01$ | −70% $p < 0.01$ | −59% $p < 0.01$ | −38% $p < 0.01$ | −43% $p < 0.01$ |
| 6 ppm | −71% $p < 0.01$ | −84% $p < 0.01$ | −74% $p < 0.01$ | −46% $p < 0.01$ | −54% $p < 0.01$ |

These results show the very interesting effect of the peptide according to the invention for moderating the secretion of pro-inflammatory mediators by NHKs having been exposed to UVB irradiation. This effect strengthens the cutaneous barrier, especially for sensitive and irritated skin and slows cutaneous aging induced by exposure to radiation and various pollutants causing microinflammation.

E) Galenic/Preparation of a Composition According to the Invention

The peptide according to the invention may be formulated with additional cosmetic active ingredients, optionally supporting and/or complementing the activity, either in the ingredient form, or at the time of producing the final cosmetic composition for the consumer. This composition may be applied to the face, body, neckline, scalp, hair, eyelashes, body hairs, in any form or vehicles known to those skilled in the art, especially in the form of solution, dispersion, emulsion, paste or powder, individually or pre-mixed or conveyed individually or as a pre-mix.

In cosmetics, applications may be proposed in particular in the skincare ranges of the face, body, hair and body hairs and makeup-care ranges.

These ingredients can be of any category depending on their function(s), the place of application (body, face, neck, bust, hands, hair, eyelashes, eyebrows, body hairs, etc.), the desired end effect and the targeted consumer, for example antioxidant, tensor, moisturizer, nourishing, protective, smoothing, remodeling, volumizing (lipofiling), acting on the radiance of the complexion, against undereye bags and dark circles, antiaging, antiwrinkles, slimming, soothing, myo-relaxing, anti-redness, anti-stretch marks, sunscreen, etc.

The CTFA ("International Cosmetic Ingredient Dictionary & Handbook" (18th Edition, 2018) published by "The Cosmetic, Toiletry, and Fragrance Association, Inc.", Washington, D.C.) describes a wide variety, without limitation, of cosmetic ingredients usually used in the skincare and scalp care industry, which are suitable for use as additional ingredients in the compositions of the present invention.

At least one of the compounds chosen from vitamin B3 compounds, compounds such as niacinamide or tocopherol, retinoid compounds such as retinol, hexamidine, α-lipoic acid, resveratrol or DHEA, hyaluronic acid, peptides, especially the N-acetyl-Tyr-Arg-O-hexadecyl, the Pal-VGVAPG (SEQ ID NO: 3), the Pal-KTTKS (SEQ ID NO: 1), the Pal-GHK, the Pal-KMO2K, the Pal-GQPR (SEQ ID NO: 2) and the Pal-K(P)HG, can be mentioned, which are active ingredients widely used in cosmetic or dermatological compositions.

Other additional skin care actives that are particularly useful can be found in Sederma's commercial literature and at www.sederma.com or www.crodarom.fr.

In reinforcing the activity on the properties of the epidermis and/or the *Stratum corneum*, the additional active agent may be chosen from the group comprising: phospholipids, the various ceramides, sphingosine, phytosphingosine, glycosphingolipids, cholesterol and its derivatives, sterols (in particular those of canola and soya), fatty acids (in particular linoleic acid, palmitic acid, lipoic acid, thioctic acid), squalane (in particular of olives), triglycerides (in particular of coconut oil), lanolin, lanolin alcohols, lanosterol, vitamin D3, tocopheryl nicotinate, various oils (in particular, argan, rose, baobab), ascorbic acid, N-acetyl cysteine and N-acetyl-L-serine, vitamin B3 compounds (such as niacinamide and nicotinic acid), panthenol, pseudofilaggrin, arginine, serine, PCA salts (pyrrolidone carboxylic acid), an extract of *Centella asiatica* leaf (titrated in madecassoside and asiaticoside), certain plant extracts (roots of wild yam, chestnut, cedar bud, Solanaceae), plankton and yeast. The following active ingredients sold by Sederma can also be mentioned: Venuceane™ (extract of *Thermus thermophilus* fermentation medium), Moist 24™ (glycolic acid extract of *Imperata cylindrica* root), Dermaxyl™ (combination of ceramide 2 and Pal-VGVAPG peptide), Senestem™ (an in vitro plant cell culture extract of *Plantago lanceolata*), Ceramide 2™ (ceramide), Ceramide HO3™ (hydroxyceramide), Optim Hyal™ (glucuronic acid oligosaccharides more or less acetylated), Meiritage™ (combination of *Bupleurum falcatum, Astragalus membranaceus, Atractylodes macrocephala* root extracts), Revidrat™ (myristyl phosphomalate), Pacifeel™ (an extract of *Mirabilis jalapa*), Hydronesis™ (from fermentation of *Salinococcus hispanicus*), unsaponifiable shea Butter™ and Citystem™ (an in vitro plant cell culture extract of *Marrubium vulgare*).

More generally, the following commercial actives can also be mentioned as examples: betain, glycerol, Actimoist Bio 2™ (Active organics), AquaCacteen™ (Mibelle AG Cosmetics), Aquaphyline™ (Silab), AquaregulK™ (Solabia), Carciline™ (Greentech), Codiavelane™ (Biotech Marine), Dermaflux™ (Arch Chemicals, Inc), Hydra'Flow™ (Sochibo), Hydromoist L™ (Symrise), RenovHyal™ (Soliance), Seamoss™ (Biotech Marine), Argireline™ (nom commercial de l'acétyl hexapeptide-3 from Lipotec), spilanthol or an extract of *Acmella oleracea* known under the trade name Gatuline Expression™, an extract of *Boswellia serrata* known under the name Boswellin™, Deepaline PVB™ (Seppic), Syn-AKE™ (Pentapharm), Ameliox™, Bioxilift™ (Silab), PhytoCellTec™Argan (Mibelle), Papilactyl D™ (Silab), Preventhelia™ (Lipotec), or one or more of the following active ingredient sold by Sederma: Subliskin™, Venuceane™, Moist 24™, Vegesome Moist 24™, Essenskin™, Juvinity™, Revidrat™, Resistem™, Chronodyn™, Kombuchka™, Chromocare™ Calmosensine™, Glycokin factor S™, Biobustyl™, Idealift™, Ceramide 2™, Ceramide A2™ Ceramide HO3™, Legance™, Intenslim™, Prodizia™, Beautifeye™, Pacifeel™, Zingerslim™ Meiritage™, Senestem™, Sebuless™, Majestem™, Apiscalp™, Rubistem™, Citystem™, Neonyca™, NG Insaponifiables de Beurre de Karité™, Majestem™, Hydronesis™ and Poretect™, or mixture thereof.

Among plant extracts (in the form of conventional extracts or prepared by an in vitro method) that can be combined with the peptide according to the invention, there may more particularly be mentioned extracts of Ivy, in particular English Ivy (*Hedera helix*), of *Bupleurum chinensis*, of *Bupleurum falcatum*, of *arnica* (*Arnica montana* L), of rosemary (*Rosmarinus officinalis* N), of marigold (*Calendula officinalis*), of sage (*Salvia officinalis* L), of ginseng (*Panax ginseng*), of *Ginko biloba*, of St.-John's-Wort (*Hypericum perforatum*), of butcher's-broom (*Ruscus aculeatus* L), of European meadowsweet (*Filipendula ulmaria* L), of big-flowered Jarva tea (*Orthosiphon stamincus benth*), of artichoke (*Cynara scolymus*), of algae (*Fucus vesiculosus*), of birch (*Betula alba*), of green tea, of *cola* nuts (*Cola nipida*), of horse-chestnut, of bamboo, of *Centella asiatica*, of heather, of *fucus*, of willow, of mouse-ear, of escine, of cangzhu, of *Chrysanthellum indicum*, of the plants of the *Armeniacea* genus, *Atractylodis platicodon*, *Sinnomenum*, *Pharbitidis*, *Flemingia*, of *Coleus* such as *C. Forskohlii*, *C. blumei*, *C. esquirolii*, *C. scutellaroides*, *C. xanthantus* and *C. Barbatus*, such as the extract of root of *Coleus barbatus*, extracts of *Ballote*, of *Guioa*, of *Davallia*, of *Terminalia*, of *Barringtonia*, of *Trema*, of *antirobia*, *cecropia*, *argania*, *dioscoreae* such as *Dioscorea opposita* or Mexican, extracts of *Ammi visnaga*, of *Siegesbeckia*, in particular *Siegesbeckia orientalis*, vegetable extracts of the family of Ericaceae, in particular bilberry extracts (*Vaccinium angustifollium*) or *Arctostaphylos uva ursi*, aloe vera, plant containing sterols (e.g., phytosterol), *Manjistha* (extracted from plants of the genus *Rubia*, particularly *Rubia cordifolia*), and Guggal (extracted from plants of the genus *Commiphora*, particularly *Commiphora mukul*), kola extract, chamomile, red clover extract, *Piper methysticum* extract (Kava Kava™ from Sederma), *Bacopa monieri* extract (Bacocalmine™ from Sederma) and sea whip extract, extracts of *Glycyrrhiza glabra*, of mulberry, of *melaleuca* (tea tree), of *Larrea divaricata*, of *Rabdosia rubescens*, of *Euglena gracilis*, of *Fibraurea recisa Hirudinea*, of *Chaparral sorghum*, of sun flower extract, of *Enantia chlorantha*, of *Mitracarpe* of *Spermacocea* genus, of *Buchu barosma*, of *Lawsonia inermis* L., of *Adiantium capillus-veneris* L., of *Chelidonium majus*, of *Luffa cylindrica*, of Japanese Mandarin (*Citrus reticulata* Blanco var. unshiu), of *Camelia sinensis*, of *Imperata cylindrica*, of Glaucium Flavum, of *Cupressus sempervirens*, of *Polygonatum multiflorum*, of *Loveyly hemsleya*, of *Sambucus nigra*, of *Phaseolus lunatus*, of *Centaurium*, of *Macrocystis pyrifera*, of *Turnera diffusa*, of *Anemarrhena asphodeloides*, of *Portulaca pilosa*, of *Humulus lupulus*, of *Coffea arabica*, of *Ilex paraguariensis*, or of *Globularia cordifolia*, of *Albizzia julibrissin*, of *Oxydendron arboretum*, of *Zingimber zerumbet* smith, of *Astragalus membranaceus*, of *Atractylodes macrocephalae*, of *Plantago lanceolata*, of *Leontopodium alpinum*, of *Mirabilis jalapa*, of *Marrubium vulgare*, of *Apium graveolens* or of orchids.

The compositions of the present invention may include one or more additional peptides, including, without limitation, di-, tri-, tetra-, penta-and hexapeptides and their derivatives. According to a particular embodiment, the concentration of the additional peptide, in the composition, ranges from $1\times10^{-7}\%$ and 20%, preferably from $1\times10^{-6}\%$ and 10%, preferably between $1\times10^{-5}\%$ and 5% by weight. The term "peptide" refers here to peptides containing 10 amino acids or less, their derivatives, isomers and complexes with other species such as a metal ion (e.g. copper, zinc, manganese, magnesium, and others). The term "peptides" refers to both natural peptides and synthetic peptides. It also refers to compositions that contain peptides and which are found in nature, and/or are commercially available.

Suitable dipeptides for use herein include but are not limited to Carnosine (βAH), YR, VW, NF, DF, KT, KC, CK, KP, KK, TT, PA, PM or PP.

Suitable tripeptides for use herein include, but are not limited to RKR, HGG, GKH, GHK, GGH, GHG, KFK, KAvaK, KβAK, KAbuK, KAcaK, KPK, KMOK, KMO$_2$K (MO$_2$ being a di-oxygenated sulfoxide methionine), KVK, PPL, PPR, SPR, QPA, LPA or SPA.

Suitable tetrapeptides for use as additional peptides herein include but are not limited to RSRK (SEQ ID NO: 6), GQPR (SEQ ID NO: 7), KTAK (SEQ ID NO: 8), KAYK (SEQ ID NO: 9) or KFYK (SEQ ID NO: 10).

Suitable pentapeptides include but are not limited to KTTKS (SEQ ID NO: 11).

Suitable hexapeptides include but are not limited to GKTTKS (SEQ ID NO: 12) and VGVAPG (SEQ ID NO: 13).

Other suitable peptides for use according to the present inventin can be selected, this list being not limitative, from: lipophilic derivatives of peptides, preferably palmitoyl (Pal) derivatives or myristoyl (Myr), and metal complexes as aforementioned (e.g. copper complex of the tripeptide HGG). Preferred dipeptides include for example N-Palmitoyl-β-Ala-His, N-Acetyl-Tyr-Arg-hexadecylester (Calmosensine™, Idealift™ from Sederma), Pal-RT or Pal-KT (Sederma). Preferred tripeptide derivatives include for example Pal-GKH and Pal-GHK (from Sederma), the copper derivative of HGG (Lamin™ from Sigma), Lipospondin (N-Elaidoyl-KFK) and its analogs of conservative substitution, N-Acetyl-RKR—NH$_2$ (Peptide CK+), N-Biot-GHK (from Sederma), Pal-KAvaK, Pal-KβAlaK, Pal-KAbuK, Pal-KAcaK, or Pal-KMO$_2$K (Matrixyl®synthe'6® from Sederma), Pal-KVK (Syn-Coll™ of DSM), and derivatives thereof.

Mention may also be made here of the anti-aging tripeptides of general Formula X-Pro*-Pro*-Xaa-Y described in WO2015181688 application with Xaa selected from Leu, Arg, Lys, Ala, Ser, and Asp, at the N-terminus, X chosen from H, —CO—R$^1$ and —SO$_2$—R$^1$ and at the C-terminal end Y chosen from OH, OR$^1$, NH$_2$, NHR$^1$ or NR$^1$R$^2$, R$^1$ and R$^2$ being, independently of one another, chosen from a alkyl, aryl, aralkyl, alkylaryl, alkoxy and aryloxy group, which may be linear, branched, cyclic, polycyclic, unsaturated, hydroxylated, carbonylated, phosphorylated and/or sulfurized, said group possibly possessing in its backbone a heteroatom particularly O, S and/or or N, and Pro* corresponding to Proline, an analogue or derivative thereof; comprising, for example, Myr-PPL—OH and Myr-PPR—OH.

Here can further be cited also the propigmenting and/or pro-mec dipeptides and tripeptides of general Formula X-(Xaa$_1$)n-Pro*-Xaa$_2$-Y disclosed in WO2014/080376, with n=0, 1 or 2, Xaa$_1$ an hydrophobic aminoacid selected from Ala, Val, Met, Leu, Iso, Phe, Pro, and analogs and derivatives thereof; or a polar aminoacid selected from Ser, Thr, Tyr, Asp, Glu and analogs and derivatives thereof; and when n=2 the two aminoacids Xaa$_1$ being the same or different; Xaa$_2$ being an hydrophobic aminoacid selected from Ala, Val, Met, Leu, Iso, Phe, and analogs and derivatives thereof, or a basic aminoacid selected from Arg, Lys, His, and analogs and derivatives thereof; at the N terminal end X being selected from H, —CO—R$_1$ and —SO$_2$—R$_1$; at the C terminal end Y being selected from OH, OR$_1$, NH$_2$, NHR$_1$ or NR$_1$R$_2$; R$_1$ and R$_2$ being, independently from each other, selected from an alkyl, aryl, aralkyl, alkylaryl, alkoxy et aryloxy group, that can be linear, branched, cyclic polycyclic, saturated, unsaturated, hydroxylated, carbonylated, phosphorylated and/or sulfured, said group having or not an O, S and/or N heteroatom in its skeleton and Pro* corresponding to a Proline, analog or derivative thereof; comprising for example the following peptides Pal-SPR—OH, Pal-PPR—OH, Pal-QPA—OH, Pal-LPAOH, Myr-SPA-OH, Pal-PM—OH, Pal-PA—OH and Pal-PP—OH.

Suitable tetrapeptide derivatives for use as additional peptides according to the present invention include, but are not limited to, Pal-GQPR (SEQ ID NO: 2) (from Sederma), Ela-KTAK (SEQ ID NO: 14), Ela-KAYK (SEQ ID NO: 15) or Ela-KFYK (SEQ ID NO: 16). Suitable pentapeptide derivatives for use as additional peptides herein include, but are not limited to, Pal-KTTKS (SEQ ID NO: 1) (available as Matrixyl® from Sederma), Pal-YGGFXaa (SEQ ID NO: 17) with Xaa being Leu or Pro, or mixtures thereof.

Suitable hexapeptide derivatives for use herein include, but are not limited to, Pal-VGVAPG (SEQ ID NO: 3), Pal-GKTTKS (SEQ ID NO: 18), Pal-HLDIIXaa with Xaa being Trp, Phe, Tyr, Tic, 7-hydroxy-Tic ou Tpi (SEQ ID NO: 19) and derivatives thereof. The mixture of Pal-GHK and Pal-GQPR (SEQ ID NO: 2) (Matrixyl® 3000, Sederma) can also be mentioned.

The preferred compositions commercially available containing a tripeptide or a derivative include Biopeptide-CL™, Maxilip™, Biobustyl™, Procapil™ and Matrixyl®synthe'6® of Sederma. The compositions commercially available preferred sources of tetrapeptides include Rigin™, Eyeliss™ Matrixyl® Reloaded and Matrixyl 3000® which contain between 50 and 500 ppm of Pal-GQPR (SEQ ID NO: 2) and an excipient, proposed by Sederma.

The following sold peptides can be mentioned as well as additional active ingredients:

Vialox™ (INCI name=Pentapeptide-3 (synthetic peptide comprising alanine, arginine, isoleucine, glycine and proline)), Syn-ake™ (β-Ala-Pro-Dab-NH-Bzl) or Syn-Coll™ (Pal-Lys-Val-Lys-OH) sold by Pentapharm;

Argireline™ (Ac-Glu-Glu-Met-Gln-Arg-Arg-NH$_2$ (INCI name=Acetyl hexapeptide-3) (SEQ ID NO: 20), Leuphasyl™ (Tyr-D-Ala-Gly-Phe-Leu) (SEQ ID NO: 21), Aldenine™ (Gly-His-Lys), Trylagen™ (INCI name=*Pseudoalteromonas* Ferment Extract, Hydro lyzed Wheat Protein, Hydro lyzed Soy Protein, Tripeptide-10 Citrulline (reaction product of Citrulline and Tripeptide-10 (synthetic peptide constituted of aspartic acid, isoleucine and lysine)), Tripeptide-1), Eyeseryl™ (Ac-β-Ala-His-Ser-His)(SEQ ID NO: 22), Serilesine™ (Ser-Ile-Lys-Val-Ala-Val) (SEQ ID NO 23) or Decorinyl™ (INCI name: Tripeptide-10 Citrulline=reaction product of Citrulline and Tripeptide-10 (synthetic peptide constituted of aspartic acid, isoleucine and lysine) sold by Lipotec;

Collaxyl™ (Gly-Pro-Gln-Gly-Pro-Gln (SEQ ID NO 24)) or Quintescine™ (Cys-Gly) sold by Vincience;

Cytokinol™LS (casein hydrolysate) sold by Les Laboratoires Serobiologiques/Cognis;

Kollaren™ (Gly-His-Lys), IP2000™ (Pal-Val-Tyr-Val) or Meliprene™ (INCI name=Monofluoroheptapeptide-1: reaction product of acetic acide and a synthetic peptide comprising arginine, glycine, glutamic acid, histidine, norleucine, p-fluorophenylalanine and tryptophan) sold by l'Institut Europeen de Biologie Cellulaire;

Neutrazen™ (Pal-His-D-Phe-Arg-NH$_2$) sold by Innovations; or

BONT-L-Peptide™ (INCI name=Palmitoyl Hexapeptide-19: reaction product of palmitic acid and Hexapeptide-19 (synthetic peptide constituted of asparagine, aspartic acid, lysine and methionine), Timp-Peptide™ (INCI name=Acetyl Hexapeptide-20: reaction product obtained by acetylation of Hexapeptide-20 (synthetic peptide constituted of alanine, glycine, lysine, valine and proline) or ECM Moduline™ (INCI name=Palmitoyl Tripeptide-28: reaction product of palmitic acid and Tripeptide-28 (synthetic peptide constituted of arginine, lysine and phenylalanine) sold by Infinitec Activos.

Different compositions/formulations according to the invention are described below with examples of additional active ingredients.

The active ingredient according to the invention is as described in point C/, that is to say comprising the vectorized peptide.

This ingredient is generally formulated in a range of 1 to 5%, preferably 3%.

1) Cream form, for example an antiageing day cream for the face.

| Raw material | INCI name | Role | % |
|---|---|---|---|
| Part A: | | | |
| H$_2$O | / | / | qsp 100 |
| Carbopol ™ Ultrez 10 | Carbomer | Thickener/Gelling | 0.30 |
| Part B: | | | |
| Brij S2-SS-(RB) ™ | Steareth-2 | Emulsifier | 0.40 |
| Brij S10-SO-(RB) ™ | Steareth-10 | Emulsifier | 1.20 |
| Crodafos CES-PA-(RB) ™ | Cetearyl Alcohol (and) Dicetyl Phosphate (and) Ceteth-10 Phosphate | Emulsifier/conditionner | 4.00 |
| Crodacol CS90-PA-(RB) | Cetearyl Alcohol | Emollient | 1.50 |
| Laurocapram | Laurocapram | Emollient | 2.50 |
| Crodamol ™ AB-LQ-(RB) | C12-15 Alkyl Benzoate | Emollient | 1.50 |
| Crodamol ™ OSU-LQ-(JP) | Diethylhexyl Succinate | Emollient | 7.00 |
| Part C: | | | |
| Glycerin | Glycerin | Humectant | 2.50 |
| Octanediol | Caprylyl Glycol | Humectant/Emollient | 0.50 |
| Parti D: | | | |
| Phenoxyethanol | Phenoxyethanol | Preservative | qs |
| Part E: | | | |
| Potassium sorbate | Potassium Sorbate | Preservative | qs |
| Part F: | | | |
| H$_2$O | / | / | 4.00 |
| NaOH 30% | Sodium Hydroxide | pH adjuster | 0.40 |
| Part G: | | | |
| Ingredient according to the invention | / | Active | 3.00 |

Example(s) of additional active ingredient(s):
1. A moisturizing/smoothing ingredient such as:
   OPTIM HYAL™, sold by Sederma, containing acetylated glucuronic acid oligosaccharides having a structure analogous to hyaluronic acid fragments.
2. A sebo-regulator ingredient such as:
   SEBULESS™, sold by Sederma, comprising an extract of *Syringa vulgaris* obtained by in vitro cell culture, which is a sebum regulator purifying, mattifying and refreshing complexion, and blurring imperfections.

PORETECT™, sold by Sederma, comprising a combination of flaxseed and celeri extracts titrated in cylolinopeptides and senkyunolides, which provides firmness, tone and density to the skin, thereby strengthening the pore-retaining structures which collapse with ageing.

3. An ingredient acting on the elastic properties of the skin/skin barrier such as:
   IDEALIFT™, sold by Sederma, comprising the N-acetyl-Tyrosyl-Arginyl-O-hexadecyl ester lipodipeptide, fighting the flaccidity of the face and improving the resistance to gravity, via in particular a elastin stimulation.

4. DERMAXYL™, sold by Sederma, combining ceramide 2, a cement of the *Stratum corneum*, and the Pal-Val-Gly-Val-Ala-Pro-Gly, a palmitoyled matrikine, which smoothes wrinkles and repairs the cutaneous barrier.

1) Mild Aqueous Serum Form

| Raw material | INCI name | Role | % |
|---|---|---|---|
| Part A: | | | |
| H₂O | / | / | qsp 100 |
| Potassium sorbate | Potassium Sorbate | Preservative | 0.10 |
| Part B: | | | |
| Glycerin | Glycerin | Humectant | 5.00 |
| Phenoxyethanol | Phenoxyethanol | Preservative | 0.80 |
| Part C: | | | |
| Cromollient ™ SCE | Di-PPG-2 Myreth-10 Adipate | Emollient | 1.20 |
| VisiaOptima ™ SE | Sodium Polyacrylate (and) Ethylhexyl Cocoate (and) PPG-3 Benzyl Ether Myristate (and) Polysorbate 20 | Rheology modifier and emulsion stabilizer | 1.00 |
| Part D: | | | |
| H₂O | / | / | 0.80 |
| NaOH 30% | Sodium Hydroxide | pH adjuster | 0.08 |
| Part C: | | | |
| Ingredient according to the invention | / | Active | 3.00 |

Example(s) of additional active ingredient(s):

1. An anti-aging ingredient such as:
   SENESTEM™, sold by Sederma, comprising plant cells obtained by in vitro cell culture of *Plantago lanceolata*, which in particular improves the viscoelastic properties of the skin and lightens senescence pigment spots.

2. An antioxidant ingredient such as:
   MAJESTEM™, sold by Sederma, based on plant cells of *leontopodium alpinum* obtained by in vitro cell culture titrated in leontopodic acid; neutralizing oxidative stress (pollution, UV radiation) and restoring skin tension.

2) Gel Form

| Raw material | INCI name | Role | % |
|---|---|---|---|
| Part A: | | | |
| H₂O | / | / | qsp 100 |
| Carbomer | / | Rheology modifier | 0.40 |
| Part B: | | | |
| Glycerin | Glycerin | Humectant | 7.00 |
| Phenoxyethanol | Phenoxyethanol | Preservative | 0.80 |
| Part C: | | | |
| H₂O | / | / | 3.00 |
| NaOH 30% | Sodium Hydroxide | pH adjuster | 0.30 |
| Part D: | | | |
| Tween ™ 20 | Polysorbate 20 | Emulsifier | 0.50 |
| Cromollient ™ SCE | Di-PPG-2 Myreth-10 Adipate | Emollient | 1.00 |
| Covi-ox ™ | Tocopherol (and) *Helianthus Annuus* (Sunflower) Seed Oil | Antioxidant | 0.40 |
| Part E: | | | |
| Ingredient according to the invention | / | Active | 3.00 |

Example(s) of additional active ingredient(s):

1. An antipollution ingredient such as:
   CITYSTEM™, sold by Sederma, based on plant cells obtained in vitro from *Marrubium vulgare* with a high Forsythoside B concentration; used against pollution attacks: makes the skin soft and smooth, refines skin texture, reduces the visibility of blackheads, leaving the skin radiant and purified.

2. A soothing ingredient for sensitive skin such as:
   PACIFEEL™, sold by Sederma, comprising an extract of *Mirabilis Jalapa*.

3. A moisturizing ingredient such as:
   AQUALANCE™, sold by Sederma, osmoprotective moisturizing active ingredient composed of homarine and erythritol.

3) Gel Form for Making a Spray Mask

| Raw material | INCI name | Role | % |
|---|---|---|---|
| Part A: | | | |
| H₂O | / | / | qsp 100 |
| Hydrotriticum PVP PE ™ | Aqua (and) Hydrolyzed Wheat Protein/ PCP Crosspolymer | Filming agent | 3.00 |
| Volarest ™ FL | Acrylates/Beheneth-25 Methacrylate Copolymer | Rheology modifier | 2.30 |
| Potassium sorbate | Potassium Sorbate | Preservative | |
| Part B: | | | |
| Glycerin | Glycerin | Humectant | 5.00 |
| Phenoxyethanol | Phenoxyethanol | Preservative | 0.80 |
| Part C: | | | |
| Crovol ™ A70 | PEG-60 Almond Glycerides | Emollient | 1.00 |
| Ethanol | Ethanol | Solvent | 5.00 |
| Covi-ox ™ | Tocopherol (and) *Helianthus Annuus* (Sunflower) Seed Oil | Antioxidant | 0.20 |
| Part D: | | | |
| H₂O | / | / | 2.50 |
| NaOH 30% | Sodium Hydroxide | pH adjuster | 0.25 |
| Part E: | | | |
| Ingredient according to the invention | | Active | 3.00 |

Example(s) of additional active ingredient(s):
1. An ingredient acting on complexion radiance such as:
    EVERMAT™, sold by Sederma, comprising a combination of an *Enantia chlorantha* extract rich in protoberberines and oleanolic acid; decreasing pore size and brightness; refining the grain of acne-prone skin.
2. An ingredient having revitalizing properties such as:
    Fruitliquid™ Kumquat™, sold by Crodarom.

4) Cream Form, for a Makeup Base

| Raw material | INCI name | Role | % |
|---|---|---|---|
| Part A: | | | |
| H₂O | / | / | qsp 100 |
| Volarest™ FL | Acrylates/Beheneth-25 Methacrylate Copolymer | Rheology mofifier | 0.90 |
| Part B: | | | |
| Arlacel™ 2121 | Sorbitan Stearate (and) Sucrose Cocoate) | Emulsifier | 4.50 |
| Part C: | | | |
| Pentylene glycol | Pentylene Glycol | Humectant | 5.00 |
| Phenoxyethanol | Phenoxyethanol | Preservative | 0.80 |
| Part D: | | | |
| Crodamol™ SSA | Decyl Isostearate (and) Isostearyl Isostearate | Emollient | 2.00 |
| Crodamol™ TN | Isotridecyl Isononanoate | Emollient | 2.00 |
| Crodamol™ AB | C12-C15 Alkyl Benzoate | Emollient | 1.50 |
| Crodamol™ GTEH | Triethylhexanoin | Emollient | 3.00 |
| Covi-ox™ | Tocopherol (and) *Helianthus Annuus* (Sunflower) Seed Oil | Antioxidant | 0.10 |
| Part D: | | | |
| Potassium sorbate | Potassium Sorbate | Preservative | 0.10 |
| Part E: | | | |
| H₂O | / | / | 2.50 |
| NaOH 30% | Sodium Hydroxide | pH adjuster | 0.25 |
| Part E: | | | |
| Ingredient according to the invention | | Active | 3.00 |

Example(s) of additional active ingredient(s):
1. An ingredient acting on dark circles under the eye/eye contours such as:
    HALOXYL™, sold by Sederma, a combination of 2 matrikines, Pal-GHK and Pal-GQPR, with N-hydroxysuccinimide and a flavonoid, the chrysin.
    EYELISS™, sold by Sederma, combining three components: hesperidin methyl chalcone, the Valyl-Tryptophan (VW) dipeptide and the Pal-GQPR lipopeptide.
    PRODIZIA™, sold by Sederma, includes an extract of *Albizia julibrissin*, which promotes the visible reduction of signs of fatigue: dark circles, undereye bags, dull complexion and drawn features, by repairing and protecting the skin from damage caused by glycation.
2. An anti-wrinkle/anti-aging ingredient based on peptide(s) such as: MATRIXYL®, MATRIXYL 3000™, MATRIXYL synthe'6™ and/or MATRIXYL Morphomics™ sold by Sederma.

F) In vivo EFFICACY TESTS

Tested product: the cream 1) of point E) of the above galenic part.

Principles:

The efficacy evaluation of the peptide according to the invention was carried out on a certain number of volunteers during the following three complementary studies:

1. A first placebo-controlled study to measure the improvement of imperfect skin and using several complementary techniques to study different parameters:
    an evaluation of imperfections carried out on standardized photographs;
    an image evaluation of moisturisation, performed with an Epsilon™ device;
    an evaluation of the skin smoothing performed with a colour camera; and
    an assessment of the corneocyte size (state of the *Stratum corneum*) by image analysis on "stripping" (detachment of cell layers on adhesive support).
2. A second study of the whole face to quantify the perceived effect on the complexion by CLCT clinical evaluation method (Color, Luminosity, Clarity, Transparency).
3. A third placebo-controlled study aimed at demonstrating the soft "polish" effect of the peptide by analyzing the homogeneity of application and the disappearance of a self-tanning product.

1/First Study

Protocol

Specific Inclusion Criteria

This study was carried out on a panel of 29 women of middle age 41 years (30-50 years), with imperfect skin to the eye, that is to say a dull/tired/scruffy complexion and/or an irregular skin texture, rough skin. On the other hand, imperfections such as rosacea, pimples or redness have been excluded.

Volunteers had to observe a 1-month wash-out period with a single moisturizer and exclude any cosmetic act of scrub or mask type, as well as any significant sunlight.

Type of Study, Duration, Applications

The study was conducted as a single blind on the face and forearms. For 6 weeks, the volunteers applied morning and evening a cream according to the invention and a contra-lateral placebo cream.

The synopsis of the study is summarized according to the following

| T0 - - - → | T6 weeks |
|---|---|
| Standardised photos | Standardised photos |
| Camera | Camera |
| Epsilon™ device | Epsilon™ device |
| Corneocyte stripping | Corneocyte stripping |

Statistics

Statistical studies were performed using Student's t-test or, if necessary, a non-parametric Wilcoxon test. Bilateral tests were performed on matched series. For the expert evaluations, Khi² tests were used.

Method and Results

Imperfection Evaluation

Standardized photos were taken at T0 and T6 weeks using a photographic bench using a high definition digital camera, a specific lighting and a system of restraint for volunteers. The position of the face, the photo and lighting settings were standardized and controlled to be reproduced over time. The obtained photos were appreciated by a panel of 5 expert judges. For each volunteer, the experts visualized the pictures before and after treatment and gave their opinion on the following statement: "the complexion has improved", that is to say the complexion is more homogeneous, the skin is smoother with less imperfections.

The results are presented below.

|  | Favorable opinion | Neutral opinion | Unfavorable opinion |
|---|---|---|---|
| Placebo | 36% | 57% | 8% |
| Invention | 54%**$ | 42% | 3% |

**Significant change compared to the unfavorable opinion with p < 0.01/
$significant variation from placebo with p < 0.05.

The application of the cream according to the invention brings a visible and significant improvement of the complexion with 54% of favorable opinions against 3% of unfavorable opinions. On the contrary, with only 36% positive and 8% negative, placebo use was clearly and significantly different (p<0.05).

Moisturisation Evaluation

An Epsilon™ E100 device (from Biox) was used. It has the distinction of providing not only a single value but an average value, over several thousand points, and also an image of moisturisation ("capacitance imaging"). Thanks to its capacitive sensor with a spatial resolution of 50 μm, the image area is 12.8×15 mm, corresponding to 76800 pixels. Each pixel gives a ε value of dielectric permittivity of the skin between 0 and 85 with as benchmarks: air=1 and water=80. The measurement depth reaches about 50 microns. In addition to the iconographic interest, this 2D measurement also allows to have information on the topography of the skin, and by extension on its homogeneity, or even potentially its suppleness since it is known that moisturisation improves this parameter.

TABLE 11

Variation of the moisturisation on the forearm (n = 3 measures, 25 volonteers)

|  | Invention | | Placebo | |
|---|---|---|---|---|
| Dielectric permitivity ∈ | T0 | T6 weeks | T0 | T6 weeks |
| Mean | 7.06 | 8.88 | 7.00 | 7.79 |
| Standard variation | 2.57 | 3.96 | 2.63 | 2.91 |
| % variation vs. T0 |  | +25.8% |  | +11.3% |
| Significance |  | p < 0.01 |  | nsd |
| Maximum |  | 99%(x2) |  |  |
| Responders |  | 80% |  |  |
| Significance vs. Placebo* |  | p < 0.05 |  |  |

*Against placebo: non-parametric lest, unilateral; p < 0.1 bilaterally.
Nsd: nonsignificant difference After 6 weeks of application of the cream according to the invention, the moisturisation value is increased by +25.8%. At the same time, the application of a placebo resulted in a smaller increase of +11.3% (since the arms are usually without cream, it is normal for the placebo to have an effect).

The images obtained with the Epsilon™ were also appreciated by a panel of 5 expert judges.

For each volunteer, the experts visualized the photos after treatment with the cream according to the invention or with the placebo cream and chose which image had the greatest homogeneity.

TABLE 12

% of favorable or unfavorable opinions concerning the skin homogeneity (n = 25 volunteers, 5 judges)

| 48%** | 41% | 11% |
|---|---|---|
| Skin more homogeneous with the cream according to the invention | Identical skins with the cream according to the invention and the placebo cream | More homogeneous skin with placebo cream |

**Significant change with regard to the "more homogeneous skin with placebo" category with p < 0.01.

On the images, each black area does not give information while each pixel gives one. The distribution of moisturisation varies between the two images: the image corresponding to the sites having received the cream according to the invention is «denser» in pixels than the image corresponding to the sites having received the placebo. This indicates that the skin, in addition to being better hydrated, has become smoother and potentially suppler.

Smoothing Evaluation

A color camera was used for this evaluation. It is a camera that uses diffused and constant LED lighting with polarization to avoid any shine. It has an image correction algorithm, which allows instant color calibration and image homogeneity (eliminates shadows at the edges). Its measurement field is 16×12 mm with a resolution of 10 million pixels. It has an ×50 zoom that allows to see structures smaller than 20 μm. In addition, thanks to a system based on the stereophotometry technique, the camera records several images under different lighting conditions, which enables the image to be reconstructed in 3D and to analyze the topography of the skin.

This last function was used for the study of the cream according to the invention and two parameters of topographies were evaluated: the complexity and the depth of the microrelief.

TABLE 13

Variation of the topography of the microrelief on the forearm (smoothing effect) (average of 2 sites, 28 volunteers)

|  | Depth of microrelief (in μm) | | | | Complexity of microrelief (in %) | | | |
|---|---|---|---|---|---|---|---|---|
|  | Invention | | Placebo | | Invention | | Placebo | |
|  | T0 | T6 weeks | T0 | T6 weeks | T0 | T6 weeks | T0 | T6 weeks |
| Mean | 24.03 | 20.96 | 23.53 | 21.54 | 0.86 | 0.68 | 0.84 | 0.72 |
| Standard deviation | 4.75 | 3.81 | 4.74 | 3.60 | 0.29 | 0.21 | 0.28 | 0.20 |
| % variation vs. T0 |  | −12.8% |  | −8.5% |  | −20.9% |  | −14.3% |

TABLE 13-continued

Variation of the topography of the microrelief on the forearm
(smoothing effect) (average of 2 sites, 28 volunteers)

| | Depth of microrelief (in µm) | | | | Complexity of microrelief (in %) | | | |
|---|---|---|---|---|---|---|---|---|
| | Invention | | Placebo | | Invention | | Placebo | |
| | T0 | T6 weeks | T0 | T6 weeks | T0 | T6 weeks | T0 | T6 weeks |
| Significance | | p < 0.01 | | p < 0.01 | | p < 0.01 | | p < 0.01 |
| Maximum | | −29% | | | | −42% | | |
| Responders | | 79% | | | | 79% | | |
| Significance vs. Placebo* | | p < 0.04 | | | | p < 0.05 | | |

*Against placebo: Parametric unilateral test; p < 0.08 and 0.05 bilaterally

Firstly, there is a smoothing effect of the placebo (−8.5% and −14.3% for each parameter), which can be explained as previously by an unusual intake of cream on this site.

However, the effect of the cream according to the invention is widely and significantly higher, whether for the depth of the microrelief (−12.8%, p<0.04 vs. placebo) or its complexity (−20.9%, p<0.05 vs. placebo).

Evaluation of Corneocytes Size

Several studies have shown that the size of corneocytes is reduced under micro-stress conditions, this being correlated with the increase in the rate of epidermis which causes some immaturity of the corneocytes.

At T0 and T6 weeks, corneocytes were harvested from volunteer skin in a standardized manner using adhesives and then labelled with a fluorescent reagent to visualize and quantify their surface under a microscope. About 300 corneocytes by volunteers and by case were quantified.

TABLE 14

Variation in the size of corneocytes on the face
(average over n = 300 corneocytes, 29 volunteers)

| Size of coneocytes | Cream according to the invention | | Placebo cream | |
|---|---|---|---|---|
| (in pixels) | T0 | T6 weeks | T0 | T6 weeks |
| Mean | 8365 | 8321 | 8499 | 8299 |
| Standard deviation | 517 | 516 | 549 | 521 |
| % variation vs. T0 | | −0.5% | | −2.4% |
| Significance | | nsd | | p < 0.01 |
| Significance vs. placebo | | p < 0.05 | | |

These results show that if the size of the corneocytes did not vary significantly between T0 and T6 weeks on the side treated with the cream according to the invention. A reduction of this size was observed (−2.4%, p<0.01) on the placebo side.

The test was conducted in autumn, season with many changes in weather and temperature. It is likely that volunteers skin "recorded" these variations as stress leading to a slight decrease in corneocyte size. The use of the cream according to the invention allowed to maintain the homeostasis of the epidermis upper part and thus to soothe it, in particular thanks to its properties of reducing pro-inflammatory mediators and strengthening the skin barrier.

2/Second Study

Protocol

Specific Inclusion Criteria

This study was conducted on a panel of 26 women of middle age 36 years (22-44 years), with a dull complexion (based on the Spincontrol Laboratory CLCT scale (Color, Luminosity, Clarity, Transparency)) and a skin of phototype I to III.

Type of Study, Duration, Applications

The study was conducted on the face. For 6 weeks, the volunteers applied morning and evening a cream according to the invention.

Statistics

For the CLCT index, a unilateral Student t test against a theoretical average was used. In the case of self-assessments by the volunteer, Khi$^2$ tests were used.

Method and Results

1/Evaluation of Complexion by CLCT

In order to evaluate the complexion, the CLCT method is based on the visual analysis by trained judges of 7 descriptors characteristic of the complexion.

Skin colour is defined by 4 shades that characterized Caucasian skins: pink-red, olive, beige, soft pink;

Luminosity is defined by the intensity of "light spots" on prominent areas of the face;

Clarity is a synthesis of skin colour uniformity and texture regularity (homogeneity); and Transparency is characterized by the ability to see through the skin and reflects its fineness.

The subject to be evaluated sits between two "daylight" lamps and wears a cape and a black charlotte to avoid any external influence. The judges evaluate the four colors from a color chart, while the other three descriptors are graded with an analog scale ranging from 0 to 100.

An "i" index is calculated from the 7 descriptors, then an "I" CLCT index is then calculated by making the delta i (T6)−i (T0). If this index is greater than 5, with a significant probability, the product can be said as effective for complexion's radiance.

TABLE 15

Variation of the complexion perception on
the face (n = 3 judges, 26 volunteers)

| | Invention | |
|---|---|---|
| CLCT indicia I | T0 | T6 weeks |
| Mean | 25.1 | 33.5 |
| Standard deviation | ±6.5 | ±7.2 |
| Difference vs. T0 | | 8.4 |
| Variation (%) | | +33.5% |

TABLE 15-continued

Variation of the complexion perception on
the face (n = 3 judges, 26 volunteers)

| CLCT indicia I | Invention | |
|---|---|---|
| | T0 | T6 weeks |
| Significance | | p < 0.01 |
| Maximum | | 16 |
| Responders (I > 5) | | 81% |

The application of the cream according to the invention for 6 weeks varied the CLCT index by +8.4 units (+33.5%, p<0.01 vs. T0), which makes it an effective product for complexion's radiance. The most significantly improved descriptors were olive (reduced by 25%), beige (reduced by 4%) and soft pink (improved by 16%, all p<0.01 vs. T0).

Evaluation of the Complexion by Self-Assesment

At the end of the 6 weeks of application of the cream according to the invention, the volunteers gave their opinion on several points.

The results show a very good perception of the product, which the volunteers find pleasant (68%), absorbing quickly (71%) and not disturbing the makeup (84%). The effect on the face is interesting with a skin hydrated and less rough (68% and 69%) but especially the impression of skin less dull (59%). All this contributes to having a more beautiful skin (66%) and a better look (62%).

3/Third study
Protocol
Specific Inclusion Criteria

This study was performed on a panel of 20 women aged 37 (20-49) with a phototype I to III skin.

Type of Study, Duration, Applications

The study was conducted in single blind on the arms. For 6 weeks, the volunteers applied morning and evening a cream according to the invention and a contra-lateral placebo cream.

Statistics

Statistical studies were performed using $Khi^2$ tests.

Method and Results

Evaluation of the Effect of "Soft Polish" by Monitoring DHA Staining (Docosahexaenoic Acid)

This study is based on the fact that before a self-tanner application, it is necessary to perform a very soft polishing or peeling of the skin in order to make it smoother and thus ensure a more uniform and long-lasting application of the skin self-tanner.

In order to demonstrate the "soft polish" effect of the cream according to the invention, the cream was applied for 6 weeks, then zones were given DHA (conventional self-tanner) and the coloration and then fading was followed by acquisition with a C-Cube™ camera.

In order to evaluate the effect on the intensity and the homogeneity of the fading between T2 days and T7 days, the images resulting from the acquisition by the C-Cube™ camera were evaluated by an expert panel. For each volunteer, the experts had to establish which image pair (cream according to the invention or placebo cream) presented the most acceptable evolution in terms of fading (less discolouration) and/or homogeneity (less small brown patches).

The results show a very clear preference for the site having received the cream according to the invention with 63% of votes compared to the 25% of votes in favor of the placebo. This result is statistically significant with p<0.01. The preparation of the skin with the cream according to the invention has therefore resulted in a soft natural smoothing of the *Stratum corneum* comparable to a physical peeling.

The invention claimed is:

1. A method for preserving or improving a condition of the epidermis in a non-therapeutic cosmetic treatment, comprising administration of a peptide having the following general Formula (1):

$$X\text{-}(Xaa)_n K^*TFK^*\text{-}(Xaa)_m\text{-}Z \quad (1)$$

wherein:
- K* is selected from a group comprising lysine K, ornithine, diaminobutyric acid or diaminopropionic acid, or a hydroxylated derivative thereof, the two K* being identical or different;
- $(Xaa)_n$ and $(Xaa)_m$ independently of each other correspond to a sequence of n or m amino acids, where each Xaa is selected independently from Gly, Ala, Pro, Val, Leu, Ile and Phe, with n and m being integers which may be equal or different between 0 and 5;
- at the N-terminal end, X is selected from H, —CO—$R^1$, —$SO_2$—$R^1$ or a biotinoyl group;
- at the C-terminal end, Z is selected from OH, $OR^1$, $NH_2$, $NHR^1$ or $NR^1R^2$; and
- wherein $R^1$ and $R^2$, independently of one another, are selected from an alkyl, aryl, aralkyl, alkylaryl, alkoxy, saccharide and aryloxy group, which may be linear, branched, cyclic, polycyclic, unsaturated, hydroxylated, carbonylated, phosphorylated, and/or sulfur-containing, wherein said group has 1 to 24 carbon atoms and/or may have in its backbone one or more O, S and/or N heteroatoms.

2. The method according to claim 1, wherein the treatment is intended to smooth skin and/or improve its moisturisation and/or improve complexion radiance and homogenization.

3. The method according to claim 1, wherein the treatment improves and/or strengthens the epidermal barrier.

4. The method according to claim 1, wherein the peptide is capable of protecting the skin from molecules and aggression of the external environment.

5. The method according to claim 1, wherein the peptide promotes desquamation of the horny layer and a natural peel of the skin.

6. The method according to claim 1, wherein the peptide is capable of stimulating production of α-crystallin to protect the skin from UV, inflammatory and oxidative type aggressions.

7. The method according to claim 1, wherein the peptide is solvated in an oil-wax-surfactant microemulsion and water so as to slow down its penetration and make it more bioavailable at the surface of the skin at the level of epidermis.

8. The method according to claim 1 to achieve a natural soft smoothing prior to the application of a self-tanning active.

9. The method according to claim 8, wherein the peptide is applied for a period of at least 3 days, before application of a self-tanning active.

10. The method according to claim 1, wherein K* is a lysine K or an ornithine.

11. The method according to claim 1, wherein n and m are independently 0 or 1 or 2.

12. The method according to claim 1, wherein the peptide is either modified in the N-terminal position or in the C-terminal position, where X=H and Z=OH being excluded.

13. The method according to claim 12, wherein $R^1$ and/or $R^2$ is an alkyl chain of 1 to 24 carbon atoms.

14. The method according to claim 12, wherein X is an acyl group CO—$R^1$ and Z is selected from OH, OMe, OEt and $NH_2$.

15. The method according to claim 1, wherein the peptide is Pal-KTFK (SEQ ID NO 5).

16. A cosmetic or dermatological ingredient comprising a peptide of the general Formula (1):

X-(Xaa)$_n$K*TFK*-(Xaa)$_m$Z       (1)

wherein:
K* is selected from the group comprising lysine K, ornithine, diaminobutyric acid or diaminopropionic acid, or a hydroxylated derivative thereof, the two K* being identical or different;
(Xaa)$_n$ and (Xaa)$_m$ correspond independently of one another to a sequence of n or m amino acids, where each Xaa is independently selected from Gly, Ala, Pro, Val, Leu, Ile and Phe, with n and m being integers which may be equal or different from 0 to 5;
at the N-terminal end, X is selected from H, —CO—$R^1$, —$SO_2$—$R^1$ or a biotinoyl group;
at the C-terminal end, Z is selected from OH, $OR^1$, $NH_2$, $NHR^1$ or $NR^1R^2$; and
$R^1$ and $R^2$, independently of one another, are selected from an alkyl, aryl, aralkyl, alkylaryl, alkoxy, saccharide and aryloxy group, which may be linear, branched, cyclic, polycyclic, unsaturated, hydroxylated, carbonylated, phosphorylated, and/or sulfur-containing, wherein said group has 1 to 24 carbon atoms and/or may have in its backbone one or more O, S and/or N heteroatoms;
and a physiologically acceptable vehicle capable of slowing penetration of said peptide into the skin to act on the epidermis.

17. The ingredient according to claim 16, wherein said vehicle is a microemulsion of oil-wax surfactants and water in which the peptide is solvated.

18. A cosmetic or dermatological composition comprising the ingredient according to claim 16.

19. A kit for performing a self-tanning cosmetic treatment comprising in separate compartments:
a) a composition according to claim 18 or a composition comprising in a physiologically acceptable medium a peptide of the following general Formula (1):

X-(Xaa)$_n$K*TFK*-(Xaa)$_m$-Z       (1)

wherein:
K* is selected from a group comprising lysine K, ornithine, diaminobutyric acid or diaminopropionic acid, or a hydroxylated derivative thereof, the two K* being identical or different;
(Xaa)$_n$ and (Xaa)$_m$ independently of each other correspond to a sequence of n or m amino acids, where each Xaa is independently selected from Gly, Ala, Pro, Val, Leu, Ile and Phe, with n and m being integers which may be equal or different between 0 and 5;
at the N-terminal end, X is selected from H, —CO—$R^1$, —$SO_2$—$R^1$ or a biotinoyl group;
at the C-terminal end, Z is selected from OH, $OR^1$, $NH_2$, $NHR^1$ or $NR^1R^2$; and
wherein $R^1$ and $R^2$, independently of one another, are selected from an alkyl, aryl, aralkyl, alkylaryl, alkoxy, saccharide and aryloxy group, which may be linear, branched, cyclic, polycyclic, unsaturated, hydroxylated, carbonylated, phosphorylated, and/or sulfur-containing, wherein said group has 1 to 24 carbon atoms and/or may have in its backbone one or more O, S and/or N heteroatoms; and
b) a composition comprising, in a physiologically acceptable medium, a self-tanning active agent.

20. A peptide of the following general Formula (1):

X-(Xaa)$_n$K*TFK*-(Xaa)$_m$-Z       (1)

wherein:
K* is selected from the group comprising lysine K, ornithine, diaminobutyric acid or diaminopropionic acid, or a hydroxylated derivative thereof, the two K* being identical or different;
(Xaa)$_n$ and (Xaa)$_m$ independently of each other correspond to a sequence of n or m amino acids, where each Xaa is independently selected from Gly, Ala, Pro, Val, Leu, Ile and Phe, with n and m being integers which may be equal or different between 0 and 5;
at the N-terminal end, X is selected from H, —CO—$R^1$, —$SO_2$—$R^1$ or a biotinoyl group;
at the C-terminal end, Z is selected from OH, $OR^1$, $NH_2$, $NHR^1$ or $NR^1R^2$; and
wherein $R^1$ and $R^2$ are, independently of one another, selected from an alkyl, aryl, aralkyl, alkylaryl, alkoxy, saccharide and aryloxy group, which may be linear, branched, cyclic, polycyclic, unsaturated, hydroxylated, carbonylated, phosphorylated, and/or sulfur-containing, wherein said group has 1 to 24 carbon atoms and/or may have in its backbone one or more O, S and/or N heteroatoms,
the peptides Pal-KTFK—OH and Ela-KTFK—OH being excluded.

21. The peptide according to claim 20, wherein K* is a lysine K or an ornithine.

22. The peptide according to claim 21, wherein n and m are independently 0 or 1 or 2.

23. The peptide according to claim 20, wherein n and m are independently 0 or 1 or 2.

24. The peptide according to claim 20, wherein the peptide is either modified in the N-terminal position or in the C-terminal position, where X=H and Z=OH being excluded.

25. The peptide according to claim 20, wherein $R^1$ and/or $R^2$ is an alkyl chain of 1 to 24 carbon atoms.

26. The peptide according to claim 20, wherein X is an acyl group CO—$R^1$ and Z is selected from OH, OMe, Oet and $NH_2$.

* * * * *